US00PP36347P2

(12) United States Plant Patent
Whitaker

(10) Patent No.: US PP36,347 P2
(45) Date of Patent: Dec. 31, 2024

(54) STRAWBERRY PLANT NAMED 'FL 20.34-183'

(50) Latin Name: ***Fragaria* x *ananassa* Duchesne**
Varietal Denomination: FL 20.34-183

(71) Applicant: Florida Foundation Seed Producers, Inc., Marianna, FL (US)

(72) Inventor: Vance Whitaker, Brandon, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/407,889

(22) Filed: Jan. 9, 2024

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

U.S. PATENT DOCUMENTS

PP25,574 P3 5/2015 Whitaker
PP30,564 P3 6/2019 Whitaker

*Primary Examiner* — Susan McCormick Ewoldt
(74) *Attorney, Agent, or Firm* — Koenig IP Works, PLLC; Katherine Koenig

(57) ABSTRACT

A new and distinct variety of strawberry (*Fragaria* x *ananassa* Duchesne), which originated from seed produced by a hand-pollinated cross between 'FL 17.24-18' and 'FL 17.17-127'. The new strawberry cultivar, named 'FL 20.34-183', can be distinguished at least by its consistently well-shaped conical fruit; high early yields and large fruit size when grown in West Central Florida or other regions that have a climate similar to that of West Central Florida.

1 Drawing Sheet

Genus and species: *Fragaria* x *ananassa* Duchesne.
Cultivar denomination: 'FL 20.34-183'.

BACKGROUND OF THE NEW CULTIVAR

The present invention relates to a new and distinct cultivar of strawberry plant (*Fragaria* x *ananassa* Duchesne) named 'FL 20.34-183.' This new strawberry plant is distinguished at least by its ability to produce fruit that have high early yields of fruit with consistent conical to cordate shape when grown in West Central Florida. Asexual propagation of 'FL20.34-183' was performed at Balm, Florida, which is also where the selection was made and where plants were tested. 'FL 20.34-183' can be contrasted with 'Florida Brilliance' (U.S. Plant Pat. No. 30,564) and 'Florida127' (U.S. Plant Pat. No. 25,574), which are the current, dominant strawberry varieties in Hillsborough County, Florida. 'FL 20.34-183' is a promising candidate for commercial success because it produces high early yields of large, evenly colored and consistently shaped fruit.

Plant Breeder's Rights for this cultivar have not been applied for. The new strawberry cultivar 'FL 20.34-183' has not been made publicly available more than one year prior to the filing of this application.

SUMMARY OF THE INVENTION

When grown in a subtropical climate during the fall, winter, or a combination thereof, the new strawberry cultivar 'FL 20.34-183' can be distinguished from all other strawberry plants by at least the following characteristics: consistently well-shaped conical to cordate fruit; large fruit size; and high early yields. The new cultivar is suited for sale as a fresh market citrus fruit and is also suitable for processing.

The new cultivar 'FL 20.34-183' originated in a strawberry breeding plot in Balm, Florida. The seed parent was 'FL 17.24-18' (unpatented), an unreleased, unpatented breeding selection with excellent fruit size and yield. The pollen parent was 'FL 17.17-127' (unpatented) an unreleased, unpatented breeding selection with excellent fruit flavor, shape and color. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'FL 20.34-183' was selection number 34 of the $34^{th}$ cross in the 2020-2021 seedling trial, and thus was given the breeding trial designation of 'FL 20.34-183.' The new cultivar 'FL 20.34-183' exhibited high early yields of consistently shaped and large fruit. 'FL 20.34-183' has been asexually propagated annually by runners; and test plantings have established that the vegetative and fruit characteristics of the propagules are identical to those of the initial daughter plants.

The new cultivar 'FL 20.34-183' can be distinguished from its seed parent 'FL 17.24-18' at least by its more intense and sweet fruit flavor and by its higher early yield which is at least 25% higher during the first week of harvest. 'FL 20.34-183' can also be distinguished from its pollen parent 'FL 17.17-127' at least by its greater fruit size which is at least 3 grams larger heavier per fruit on average and its greater total yields which are at least 15% greater.

Currently, 'Florida Brilliance' (U.S. Plant Pat. No. 30,564) and 'Florida127' (U.S. Plant Pat. No. 25,574), are the two dominant strawberries varieties in Hillsborough County, Florida. The new cultivar 'FL 20.34-183' has larger fruit size than 'Florida Brilliance' (Table 1), but with higher total yields than 'Florida127' (Table 1). The November and December yields of 'FL 20.34-183' are also higher than both commercial standards (Table 1).

The new cultivar 'FL 20.34-183' is more resistant to *Phytophthora* root and crown rots (caused by *Phytophthora cactorum*) than both commercial varieties 'Florida Brilliance' and 'Florida127', but is more susceptible to crown rot (caused by *Colletotrichum gloeosporioides*) than these commercial varieties.

DESCRIPTION OF THE FIGURES

The accompanying photograph shows fruit from a 5-month-old specimen of the new strawberry cultivar 'FL 20.34-183'. These photographs show the colors as true as can be reasonably captured by conventional photographic procedures. Colors in the photographs may differ slightly from the color values cited in the detailed botanical description, which accurately describe the colors of the new strawberry cultivar. The photograph was captured in March of 2023 in West Central Florida.

FIG. 1 shows fruit from 5-month-old plants at varying stages of ripeness.

DETAILED BOTANICAL DESCRIPTION OF THE CULTIVAR

The following detailed botanical description sets forth the distinctive characteristics of the new strawberry cultivar 'FL 20.34-183'. The present botanical description is of 'FL 20.34-183' when grown under the ecological conditions that prevail during the winter production season in Balm, Florida, i.e., warm days and cool nights. Colors are objectively described using the CIELAB color scale (originally published by the International Commission on Illumination (CIE) in 1976) as measured using a Minolta Chroma Meter CR-400 (Minolta, Ramsey, NJ) colorimeter with a 1 cm aperture, calibrated against a white tile (Y=85.5, x=0.3164, y=0.3237). When the CIELAB color designations differ from the accompanying photographs, the CIELAB color designations are accurate.

Botanical Description

Botanical classification:

*Family*: Rosaceae.

*Botanical name*: *Fragaria* x *ananassa* Duchesne.

*Common name*.—Strawberry.

*Cultivar*.—'FL 20.34-183'.

Parentage:

*Female or seed parent*.—'FL 17.24-18'.

*Male or pollen parent*.—'FL 17.17-127'.

Plant description:

*Average height*.—25 cm to 30 cm.

*Average width*.—42 cm to 47 cm.

*Growth habit*.—Semi-upright.

*Number of crowns per plant*.—6 to 9, depending on seasonal conditions.

*Vigor*.—Medium.

Leaves:

*Overall description*.—Pinnately compound with three leaflets.

*Petiole*.—Average length: Approximately 19.6 cm. Average diameter: Approximately 3.3 mm. Pubescence: Light. Pubescence density: Sparse to Medium. Pose of hairs: Perpendicular. Texture: Smooth. Anthocyanin presence: Absent. Color: Light green (L*=51.31, a*=−18.79, b*=37.13).

*Petiolule*.—Length, terminal leaflet: Approximately 12.5 mm. Length, lateral leaflets: Approximately 7.0 mm. Diameter: Approximately 1.0 mm. Color: Light green (L*=47.84, a*=−12.19, b*=28.86).

*Stipule*.—Length: 41 mm to 45 mm. Width: 15-25 mm along the base of the petiole attachment. Anthocyanin presence: Absent. Color: Light green (L*=70.61, a*=−10.04, b*=27.65).

*Terminal leaflet*.—Average length: Approximately 68 mm. Average breadth: Approximately 58 mm. Length/width ratio: Approximately 1.17. Shape in cross section: Slightly concave. Color, upper surface: Medium-light green (L*=37.55, a*=−14.68, b*=19.31). Color, lower surface: Light green (L*=51.41, a*=−13.15, b*=22.23). Glossiness: Slight gloss. Base shape: Cuneate. Apex descriptor: Rounded. Pubescence density: Sparse to moderate. Texture: Moderately smooth. Venation pattern: Pinnate.

*Secondary leaflets*.—Average length: Approximately 67 mm. Average breadth: Approximately 64 mm. Length/width ratio: Approximately 1.05. Shape in cross section: Slightly concave. Color, upper surface: Medium-light green (L*=37.84, a*=−14.95, b*=19.85). Color, lower surface: Light green (L*=51.18, a*=−14.10, b*=21.70). Glossiness: Slight gloss. Base shape: Oblique rounded. Apex descriptor: Obtuse. Pubescence density: Sparse to moderate. Texture: Moderately smooth. Venation pattern: Pinnate.

*Leaflet margins*.—Crenate, with an average of 23 and 28 serrations per terminal and secondary leaflet, respectively.

Stolons:

*Number of daughter plants*.—15 to 40, depending on environmental conditions.

*Anthocyanin presence*.—Occasional.

*Thickness*.—2 mm to 3 mm.

*Pubescence*.—Light with pose of hairs ascending.

*Color*.—Similar to stolon color of 'Florida Brilliance'.

Inflorescences:

*Time of flowering*.—Partial remontancy, commencing two weeks after establishment and continually thereafter in suitable climate.

*Flower number per plant*.—45 to 60 flowers over a 4-month Florida growing season.

*Flower height*.—0 to 18 cm above soil surface depending on angle of pedicel.

*Position relative to canopy*.—Flowers open slightly below canopy height.

*Branching of the inflorescence*.—At or very close to the crown.

*Petals*.—Number: Approximately 5. Length: Approximately 11 mm. Width: 10 to 11 mm. Shape: Orbicular. Apex: Rounded. Base: Rounded. Margin: Smooth. Average diameter of the corolla (i.e. the petals collectively): 34 mm. Average number of stamens: 25. Color, upper surface: White (L*=80.87, a*=−2.12, b*=4.48). Color, lower surface: White (L*=81.86, a*=−3.59, b*=8.58).

*Calyx*.—Diameter: 35-40 mm. Diameter of calyx relative to corolla: 0%-10% greater in diameter. Diameter of calyx relative to the fruit: 0%-10% greater in diameter. Insertion of calyx: Level to slightly inserted. Color: Medium-light green (L*=53.77, a*=−12.94, b*=31.66).

*Sepals*.—Number per flower: 10-11. Length: 13-16 mm. Width: 6-7 mm. Apex: Subacute to lobed. Margin: Smooth. Color, upper surface: Medium green (L*=40.71, a*=−18.69, b*=26.34). Color, lower surface: Light green (L*=52.39, a*=−15.41, b*=24.46).

*Pedicels*.—Attached to mature primary fruit and 14 cm to 24 cm in length and 2 to 3 mm in diameter depending on the time of the season. At peak production, the plant will have several crowns, each producing a truss. Each truss will have 5 to 8 pedicels. Inflorescences branch very close to the crown, rendering the peduncle rarely visible.

Fruit:

*Number per truss*.—5 to 7.

*Shape*.—Consistently conical, with some fruit being cordate.

*Average fruit weight*.—25 to 28 g (as shown in Table 1).

*Weight, primary fruit*.—30 to 50 g.

*Weight, secondary and tertiary fruit*.—16 to 35 g.

*Length, primary fruit*.—47 to 57 mm.

*Width, primary fruit*.—42 to 47 mm.

*Fruit flavor*.—Slightly higher sweetness and flavor compared to 'Florida Brilliance'.

*Fruit firmness*.—Similar to commercial standard 'Florida Brilliance'.

*Fruit cavity*.—Rare.

*Achenes*.—Slightly sunken, 120 to 300 per fruit.

*External fruit color*.—Glossy medium red (a*=35.94).

*Internal fruit color*.—Medium red (a*=24.78).

*Evenness of color*.—Very consistently even.

*Flesh and skin firmness at full ripe stage*.—Very firm.

*Rain damage*.—Similar to 'Florida Brilliance'.

Early yield: Similar to 'Florida Brilliance' (as shown in Table 1).

Preferred planting period: October 10$^{th}$ to October 20$^{th}$ in West Central Florida.

Nursery performance: Produces similar runners to commercial standards of known varieties.

Disease resistance:

*Phytophthora crown rot* (*caused by Phytophthora cactorum*).—Moderately resistant.

*Powdery mildew* (*caused by Podosphaera aphanis*).—Moderately resistant.

*Anthracnose fruit rot* (*caused by Colletotrichum acutatum*).—Moderately resistant.

*Charcoal rot* (*caused by Macrophomina phaseolina*).—Moderately susceptible.

TABLE 1

Performance of three strawberry genotypes during the 2022-2023 season in Balm, Florida

| | Marketable yield (g/plant) | | | |
|---|---|---|---|---|
| Cultivar | November 2022-2023 | December | January | February |
| 'FL Brilliance' | 15.9 b[y] | 78.2 ab | 185.5 a | 592.5 a |
| 'Florida127' | 22.6 ab | 66.7 b | 162.0 a | 534.1 a |
| 'FL 20.34-183' | 30.1 a | 89.0 a | 188.4 a | 514.5 a |

| | Marketable yield (g/plant) | | |
|---|---|---|---|
| Cultivar | March | Total | Wt/ fruit(g) [z] |
| 'FL Brilliance' | 348.7 a | 1220.8 a | 24.9 b |
| 'Florida127' | 203.8 b | 989.2 b | 28.2 a |
| 'FL 20.34-183' | 345.3 a | 1167.3 a | 26.6 ab |

[z] Mean fruit weight was determined by dividing total marketable fruit yield per plot by total marketable fruit number per plot.
[y] Mean separation within columns is by Tukey's HSD test, $P \leq 0.05$.

What is claimed is:

1. A new and distinct strawberry plant named 'FL 20.34-183' as illustrated and described herein.

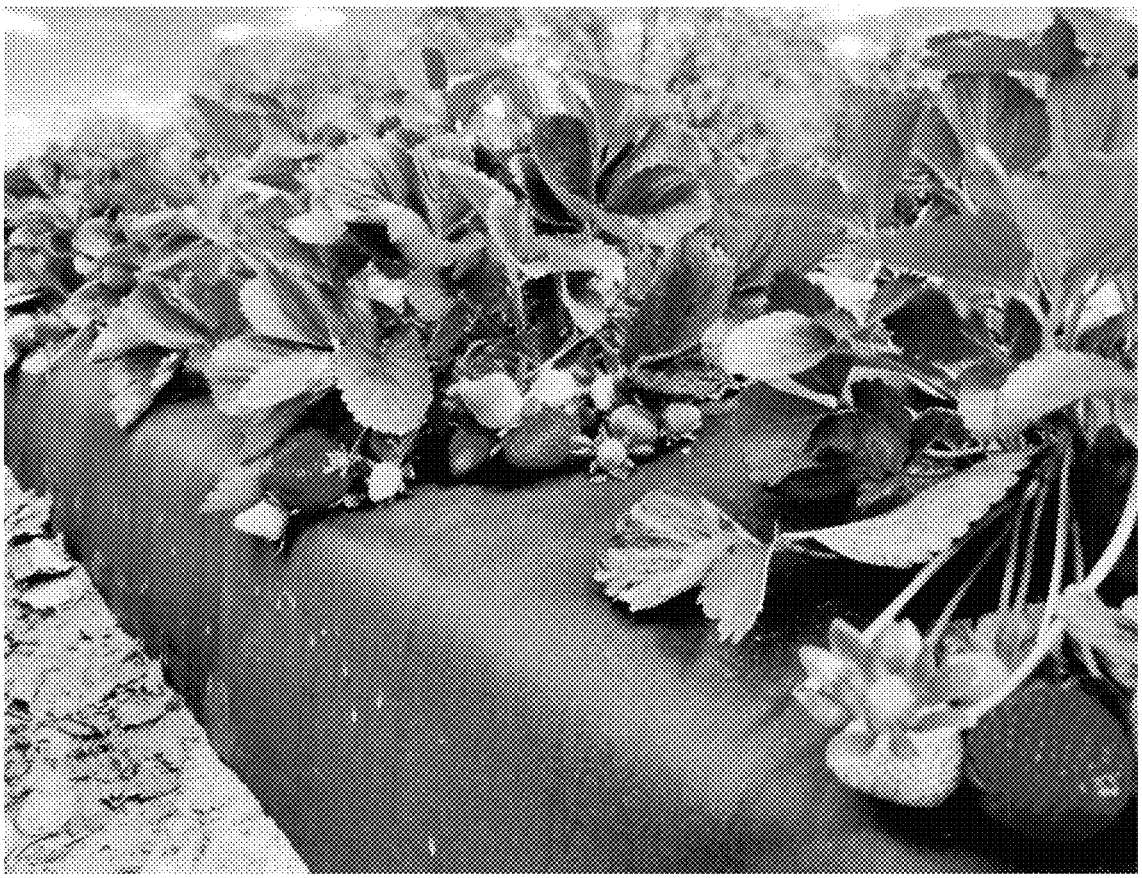

* * * * *